US008535368B2

(12) United States Patent
Headley, Jr. et al.

(10) Patent No.: US 8,535,368 B2
(45) Date of Patent: Sep. 17, 2013

(54) APPARATUS FOR LOADING AND DELIVERING A STENT

(75) Inventors: F. Anthony Headley, Jr., Marlborough, MA (US); John Damarati, Marlborough, MA (US); Gary J. Leanna, Holden, MA (US); Mark Wood, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1318 days.

(21) Appl. No.: 11/437,889

(22) Filed: May 19, 2006

(65) Prior Publication Data

US 2007/0270932 A1 Nov. 22, 2007

(51) Int. Cl.
*A61F 2/06* (2006.01)

(52) U.S. Cl.
USPC .......................................... 623/1.12

(58) Field of Classification Search
USPC ................ 623/1.12, 1.11; 606/108, 198, 200
See application file for complete search history.

(56) References Cited

U.S. PATENT DOCUMENTS

| | | | | |
|---|---|---|---|---|
| 5,645,559 A * | 7/1997 | Hachtman et al. | ............ | 623/1.2 |
| 5,683,451 A * | 11/1997 | Lenker et al. | ................ | 623/1.11 |
| 5,749,921 A * | 5/1998 | Lenker et al. | ................ | 623/1.42 |
| 5,906,619 A * | 5/1999 | Olson et al. | .................. | 606/108 |
| 6,645,239 B1 * | 11/2003 | Park et al. | .................... | 623/1.11 |
| 6,902,575 B2 * | 6/2005 | Laakso et al. | ................ | 623/1.11 |
| 6,945,990 B2 * | 9/2005 | Greenan | ....................... | 623/1.12 |
| 2003/0040789 A1 * | 2/2003 | Colgan et al. | ................ | 623/1.11 |
| 2003/0199821 A1 * | 10/2003 | Gerdts et al. | ............. | 604/103.04 |
| 2004/0167606 A1 * | 8/2004 | Chouinard | ................... | 623/1.13 |
| 2004/0230284 A1 * | 11/2004 | Headley et al. | ............. | 623/1.11 |
| 2006/0184226 A1 * | 8/2006 | Austin | ........................ | 623/1.11 |

FOREIGN PATENT DOCUMENTS

| | | |
|---|---|---|
| JP | 2002510525 A | 4/2002 |
| WO | 9951166 A1 | 10/1999 |
| WO | 0041525 A2 | 7/2000 |
| WO | 2006088638 A1 | 8/2006 |

* cited by examiner

*Primary Examiner* — Ryan Severson
*Assistant Examiner* — David Eastwood
(74) *Attorney, Agent, or Firm* — Vidas, Arrett & Steinkraus, P.A.

(57) ABSTRACT

A stent loading and deployment device includes an outer elongate tubular member having opposed proximal and distal ends and an inner elongate tubular member having opposed proximal and distal ends and slidably disposed within the outer tubular member. When the distal ends of the outer tubular member and the inner tubular member are axially aligned, a stent deployment region is defined there in between. The device further includes a stent loading member having opposed proximal and distal ends and slidably disposed between the outer tubular member and the inner tubular member. The distal end of the stent loading member is slidable to a distal position past the distal end of the outer tubular member for receiving a stent and is further slidable toward the proximal end of the outer tubular member to a location past the stent deployment region for disengagement of a stent from the stent loading member.

35 Claims, 8 Drawing Sheets

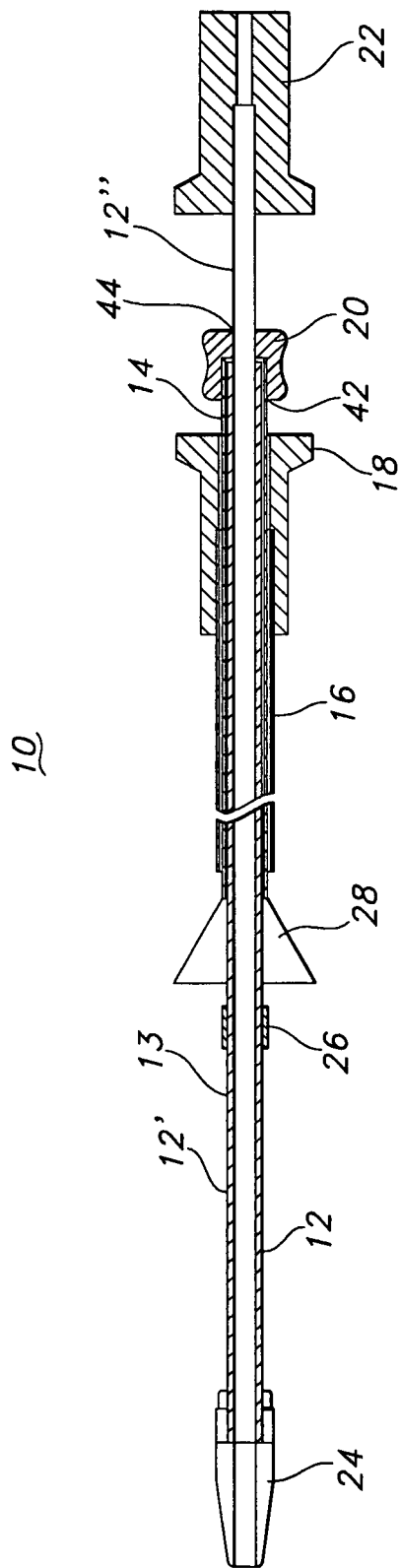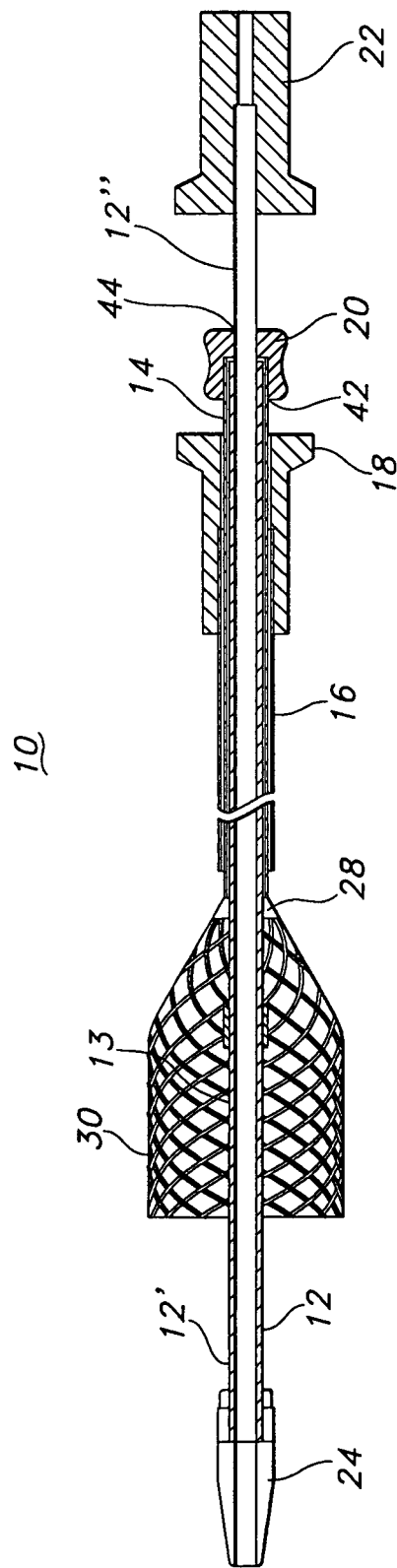

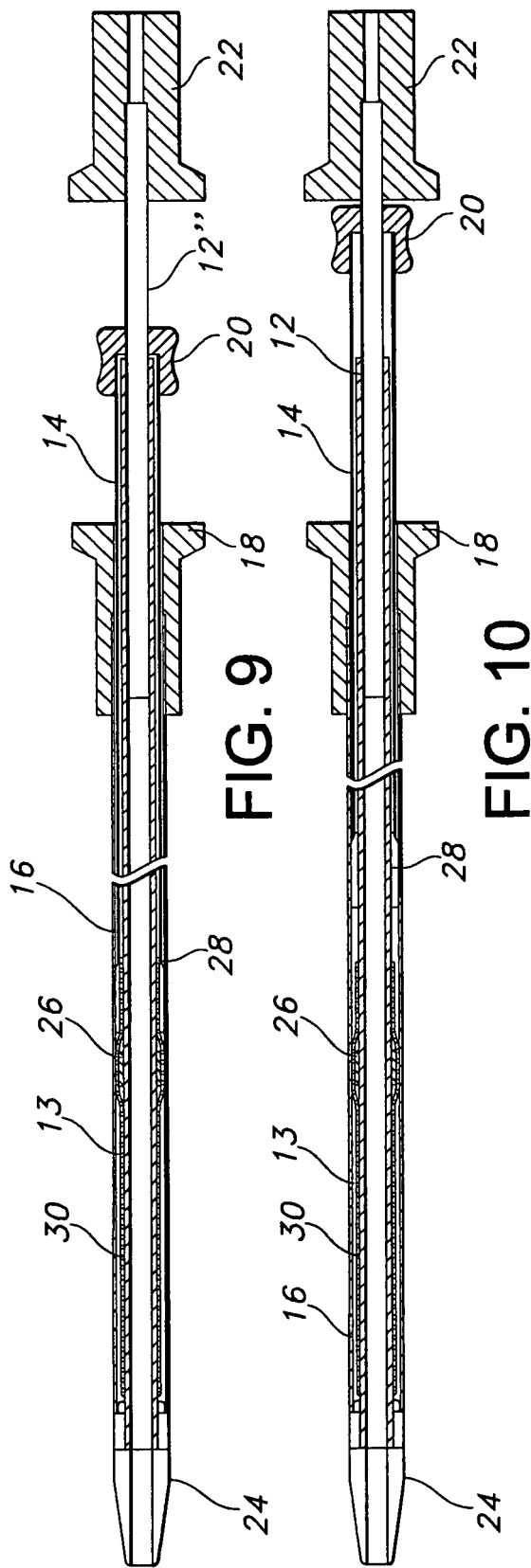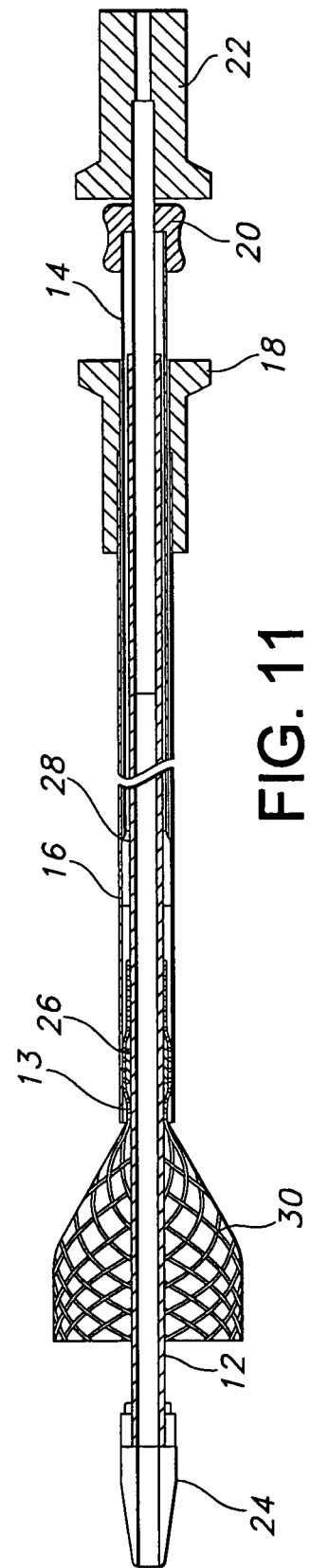

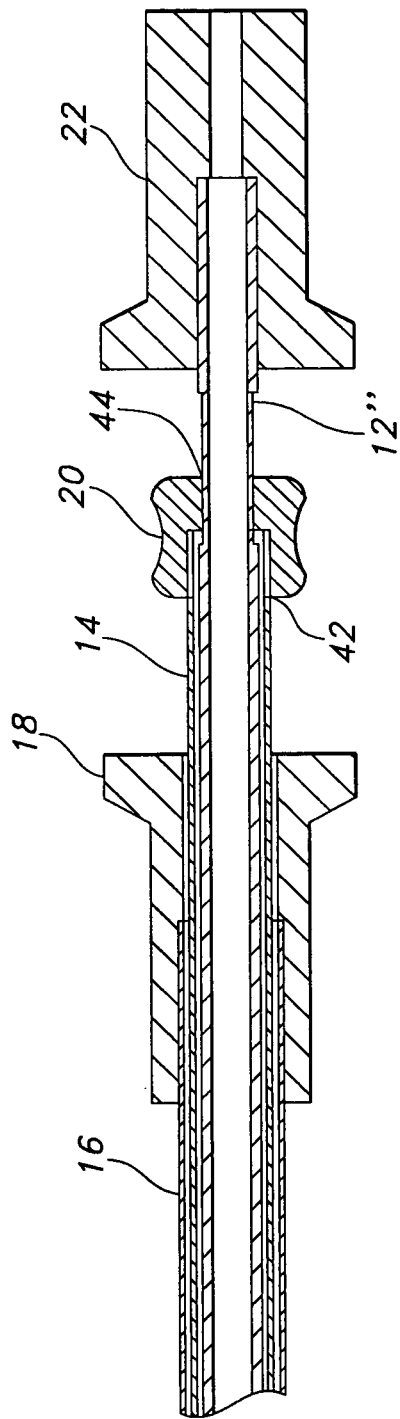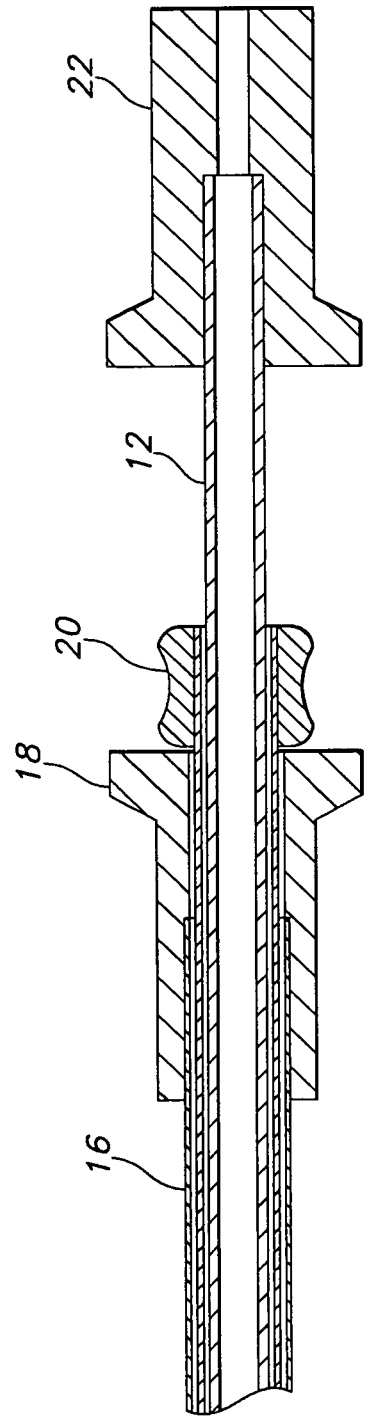
FIG. 12
FIG. 13

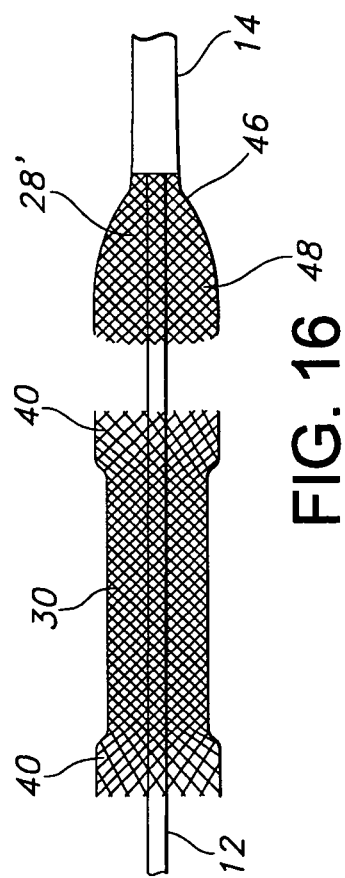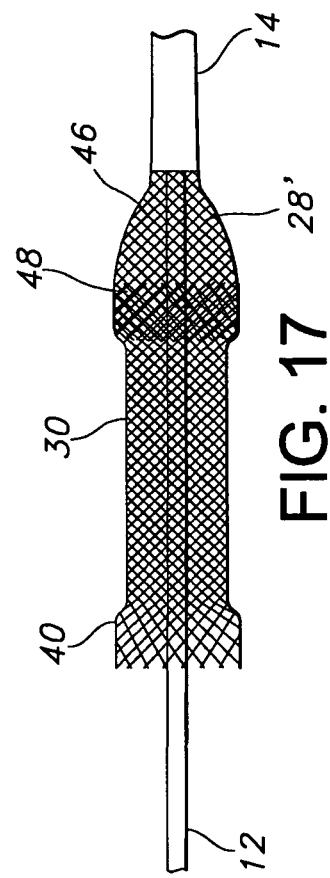

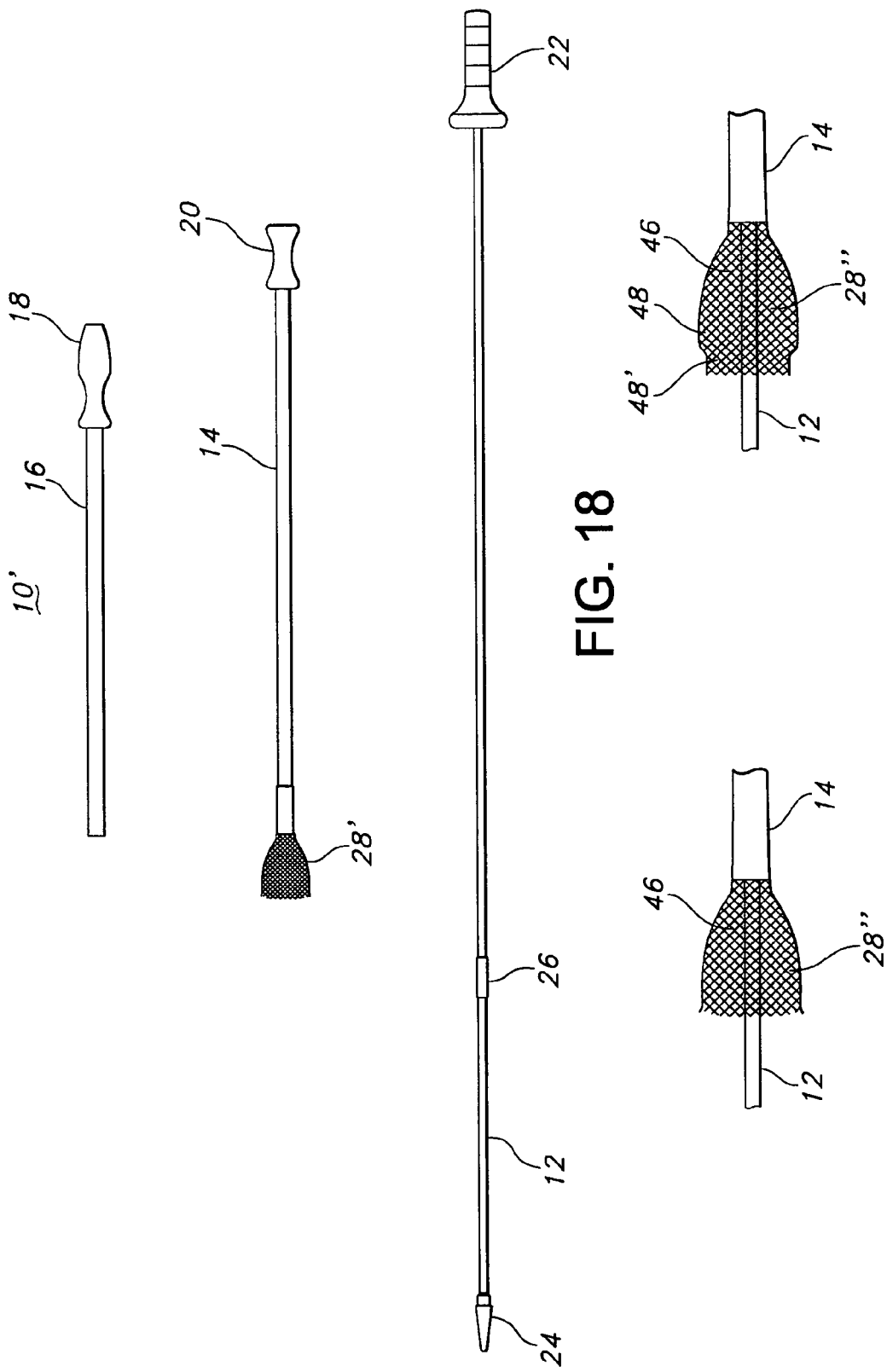

APPARATUS FOR LOADING AND DELIVERING A STENT

FIELD OF THE INVENTION

This invention relates to a method and system for transporting, loading and delivering a stent, as well as stent delivery assemblies. More particularly, this invention relates to methods and systems for loading and delivering radially distensible stents, including polymeric and non-polymeric stents.

BACKGROUND OF THE INVENTION

An intraluminary prosthesis is a medical device used in the treatment of diseased bodily lumens. One type of intraluminary prosthesis used in the repair and/or treatment of diseases in various body vessels is a stent. A stent is generally a longitudinal tubular device formed of biocompatible material which is useful to open and support various lumens in the body. For example, stents may be used in the bodily vessel, such as in the coronary or peripheral vasculature, esophagus, trachea, bronchi colon, biliary tract, urinary tract, prostate, brain, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminary catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminary vascular stents, have included helically wound coils which may have undulations or zig-zags therein, slotted stents, ring stents, braided stents and open mesh wire stents, to name a few. Super-elastic materials and metallic shape memory materials have also been used to form stents.

Although stent delivery systems are well-known in the art, the assembly of such delivery systems is often complicated. Additionally, contemporary Endoscopy practitioners increasingly use plastic self-expanding stents. Unlike most metallic self-expanding stents, the plastic ones have a tendency to permanently deform or lose some of their ability to self-expand when stored in a compressed state for a prolonged period of time. These stents are therefore preferably loaded into the stent delivery system shortly before being implanted in a patient. However, such loading often involves numerous steps and requires the use of multiple components (e.g., tools and fixtures) that are not part of the stent delivery system. Also, even with these added devices, the physician or user is often required to finish the loading process by pushing the stent into the delivery system by hand. Loading a stent in this way is therefore often difficult, time-consuming and has the potential to damage the stent. Accordingly, there is a need for simplified methods of on-site loading of a stent into stent delivery systems, while minimizing the risk of damaging the stent in the process.

SUMMARY OF THE INVENTION

The present invention is directed to a method and system for delivering a self-expanding stent into a body lumen. In particular, the present invention relates to an assembly and a method for protecting, loading and delivering a stent in combination with a stent delivery catheter, as well as to overall stent delivery systems.

In one aspect of the present invention a stent loading and deployment device is provided. The device includes an outer elongate tubular member having opposed proximal and distal ends; an inner elongate tubular member having opposed proximal and distal ends and slidably disposed within the outer tubular member, wherein, when the distal ends of the outer tubular member and the inner tubular member are axially aligned, a stent deployment region is defined there in between; and a stent loading member having opposed proximal and distal ends and slidably disposed between the outer tubular member and the inner tubular member. Desirably, the distal end of the stent loading member is slidable to a distal position past the distal end of the outer tubular member for receiving a stent and is further slidable toward the proximal end of the outer tubular member to a location past the stent deployment region for disengagement of a stent from the stent loading member. The outer elongate tubular member, the inner elongate tubular member and/or the stent loading member may be axially movable or slidable independently of each other or may be axially movable or slidable in concert in either total or in different combinations of pairs. For example, the distal end of the stent loading member my be slidable to a distal position past the distal end of the outer tubular member while the positions of the inner and outer tubular members are kept constant or relatively constant and is further slidable toward the proximal end of the outer tubular member to a location past the stent deployment region while the positions of the inner and outer tubular members are kept constant or relatively constant.

The device may further include a stent engaging member having opposed proximal and distal ends. Desirably, the proximal end is securably disposed to the distal end of the stent loading member. The stent engaging member may have a truncated-conical shape, outwardly diverging in a distal direction from its proximal end. The stent engaging member may be a thin film which is collapsible such that the stent engaging member may be slidably contained within the outer tubular member, or may be a radially distensible member which is collapsible such that the stent engaging member may be slidably contained within the outer tubular member. Desirably, the stent engaging member is a polymeric member. The stent engaging member may include, in part or substantially, braided polymeric filaments. The braided filaments may be contained within a thin polymeric film. Desirably, the stent loading member is an elongate tubular device.

The device may further include a tubular band disposed toward the distal end of the inner tubular member for releasably securing a stent in the stent deployment region between the inner and outer tubular members. Desirably, the outer tubular member is slidable toward a proximal position for releasing the stent from the stent deployment region. Typically, the outer tubular member is slid while the inner tubular member and the stent engaging member are fixed or not in substantial movement.

The device may further include an outer tubular handle disposed at the proximal end of the outer tubular member; an inner tubular handle disposed at the proximal end of the inner tubular member; and a stent loading member handle disposed at the distal end of the stent loading member. The stent loading member handle may be axially disposed between the outer tubular handle and the inner tubular handle. The outer member handle may be axially disposed before the proximal end of the inner tubular member. The handles may separated, mechanically mated, including temporarily mated or locked, and/or integrated to allow independent or non-independent axial movement or sliding the of the outer elongate tubular member, the inner elongate tubular member and/or the stent loading member The device of this aspect is useful containing and releasing a radially distensible stent. The radially distensible stent may be a polymeric stent, including a braided stent. A graft, such as a covering, a liner, a film, a coating and combinations thereof, may be disposed over at least a portion of the stent. Desirably, the stent is a braided polymeric stent and the graft is a silicone coating or film.

In another aspect of the present invention, a stent loading and deployment system is provided. The system includes a radially distensible stent; an outer elongate tubular member having opposed proximal and distal ends; an inner elongate tubular member having opposed proximal and distal ends and slidably disposed within the outer tubular member, wherein, when the distal ends of the outer tubular member and the inner tubular member are axially aligned, a stent deployment region is defined there in between; and a stent loading member having opposed proximal and distal ends and slidably disposed between the outer tubular member and the inner tubular member; wherein the distal end of the stent loading member is slidable to a distal position past the distal end of the outer tubular member for receiving the stent and is further slidable toward the proximal end of the outer tubular member to a location past the stent deployment region for disengagement of the stent from the stent loading member.

A method for loading a stent into a delivery and deployment device includes providing a radially distensible stent having opposed proximal and distal ends; providing a delivery deployment device, the device including an outer elongate tubular member having opposed proximal and distal ends; an inner elongate tubular member having opposed proximal and distal ends and slidably disposed within the outer tubular member, wherein, when the distal ends of the outer tubular member and the inner tubular member are axially aligned, a stent deployment region is defined there in between; a stent loading member having opposed proximal and distal ends and slidably disposed between the outer tubular member and the inner tubular member; and a stent engaging member having opposed proximal and distal ends, wherein the proximal end of the stent engaging member is securably disposed to the distal end of the stent loading member; axially moving or sliding the distal end of the stent loading member to a distal position past the distal end of the outer tubular member; engaging the proximal end of the stent with the stent engaging member; axially moving or sliding the stent and the stent loading member toward the proximal end of the outer tubular member to radially compress the stent within the stent deployment region; and axially moving or sliding the stent engaging member to a location past the stent deployment region for disengagement of the stent from the stent loading member. The method may further include providing a tubular band disposed toward the distal end of the inner tubular member for releasably securing the stent in the stent deployment region between the inner and outer tubular members. Moreover, the method may further include axially moving or sliding the outer tubular member toward a proximal position for releasing the stent from the stent deployment region. The method may yet further include providing an outer tubular handle disposed at the proximal end of the outer tubular member; providing an inner tubular handle disposed at the proximal end of the inner tubular member; and providing a stent loading member handle disposed at the proximal end of the stent loading member, wherein independent axial movement of the outer tubular member, the inner tubular member or the stent loading member is achieved by manual manipulation of the handles.

These and other objectives, features, and advantages of this invention will become apparent from the following detailed description of illustrative embodiments thereof, which is to be read in connection with the accompanying drawings.

BRIEF DESCRIPTION OF THE DRAWINGS

FIG. 1 is a cross-sectional view of an embodiment of a stent loading and delivery device or system of the present invention.

FIG. 2 is a cross-sectional view of the stent loading and delivery device or system of FIG. 1 illustrating an initial stage of loading a stent into the device or system.

FIG. 9 is a cross-sectional view of the stent loading and delivery device or system of FIG. 1 illustrating a fully loaded a stent therein.

FIG. 10 is a cross-sectional view of the stent loading and delivery device or system of FIG. 9 illustrating disengagement of the stent from a stent loading mechanism.

FIG. 11 is a cross-sectional view of the stent loading and delivery device or system of FIG. 10 illustrating the initial deployment of the stent.

FIG. 12 is an exploded cross-sectional view of the proximal portion of the stent loading and delivery device or system of FIG. 1.

FIG. 13 is an exploded cross-sectional view of an alternative embodiment of the proximal portion of the stent loading and delivery device or system of FIG. 1.

FIGS. 16 and 17 are exploded top planar views of the stent and the stent engaging portion of the stent loading and delivery device or system of FIGS. 14-15.

FIG. 18 is a top planar view of different elements of the stent loading and delivery device or system of FIG. 14 in a dissembled configuration.

FIGS. 19 and 20 are alternate embodiments of the stent engaging portion of FIG. 16.

DETAILED DESCRIPTION OF THE INVENTION

Figure 3:
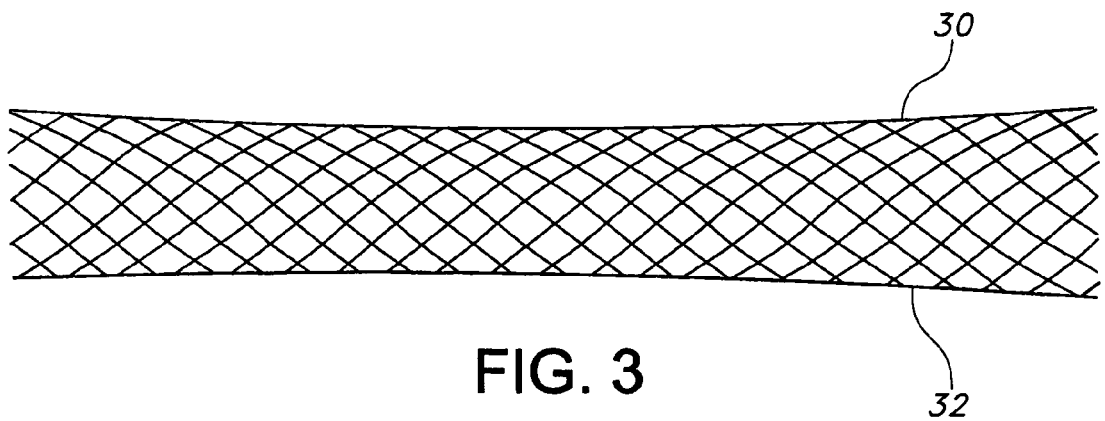
FIG. 3 is an exploded view of the stent of FIG. 2.

The present invention relates to an assembly and method for transporting and deploying a stent, or other intraluminary member as described herein, in a bodily passageway. The assembly is suited for medical applications (particularly, endoscopic therapy) in the gastrointestinal tract, the biliary tract, the urinary tract, and the respiratory tract. In particular, a preferred embodiment of the present invention is directed to an assembly and method for transporting, loading and delivering a self-expanding esophageal stent. The system allows the clinician or user to easily load a stent into a delivery system with minimal effort and without damaging the stent. The assembly in accordance with the present invention, however, could also be used in the neurological system (e.g., in the brain), the vascular system (e.g., in arteries or veins), in the cardiovascular system (e.g., in the heart) and in the like. Reference to bodily passageways may be to passageways in any of the aforementioned tracts and systems or elsewhere in the body.

References herein to the term "distal" and variants thereof refer to a direction away from an operator of the subject invention, while references to the term "proximal" and variants thereof refer to a direction towards the operator of the subject invention. Accordingly, when the terms "distal" and "proximal" are used herein in the context of an assembly device that is being deployed within a body, such as a human body, by an operator, the term "distal" refers to a location within or near the body that is further within the body than a location that is "proximal" to the operator.

FIG. 1 is a cross-sectional view of a stent loading and delivery system or device 10 according to the present invention. The system 10 is particularly well suited for the loading, transluminal delivery and intraluminal deployment of a radially self-expanding prosthesis, such as a stent and/or a stent-graft. The system 10 includes an elongate, flexible inner tubular member 12, an intermediate tubular member 14, which may also be also referred to as a stent loading member 14, and an outer tubular member 16, interrelated as shown. An outer tubular handle 18 is disposed at the proximal end of the outer tubular member 16. An intermediate tubular handle 20 is disposed at the proximal end of the intermediate tubular member 14. An inner tubular handle 22 is disposed at the proximal end of the inner tubular member 12. Manipulation or axial movement of the handles 18, 20 and 22 permits independent axial movement of the tubular members 12, 14, 16, respectively. For example, the intermediate tubular handle 20 may be axially moved between distal and proximal positions to so axially move the intermediate tubular member 14. Such movement may be done while keeping the other handles 18, 22 fixed or relatively fixed to allow independent or substantially independent movement of the intermediate tubular member 14 while the inner tubular member 12 and the outer tubular member 16 remain fixed or relatively fixed. In a similar fashion, the outer tubular handle 18 may be axially moved between distal and proximal positions to so axially move the outer tubular member 16 while keeping the other handles 20, 22 fixed or relatively fixed to allow independent or substantially independent movement of the outer tubular member 16 while the inner tubular member 12 and the intermediate tubular member 14 remain fixed or relatively fixed. Moreover, the inner tubular handle 22 may be axially moved between distal and proximal positions to so axially move the inner tubular member 12 while keeping the other handles 18, 20 fixed or relatively fixed to allow independent or substantially independent movement of the inner tubular member 12 while the outer tubular member 16 and the intermediate tubular member 14 remain fixed or relatively fixed. Further, the handles 18, 20 and 22 may be moved or manipulated in concert as a pair while keeping the third or non-paired handle fixed or relatively fixed to allow concurrent movement of two tubular members while keeping the third tubular member fixed or relatively fixed. For example, the outer tubular member 16 and the intermediate tubular member 14 may be moved in concert while keeping the inner tubular member 12 fixed or relatively fixed by manipulating the outer tubular handle 18 and the intermediate tubular handle 20 in concert while keeping the inner tubular handle 22 fixed or relatively fixed. Further, the outer tubular member 16 and the inner tubular member 12 may be moved in concert while the intermediate tubular member 14 keeping fixed or relatively fixed by manipulating the outer tubular handle 18 and the inner tubular handle 22 in concert while keeping the intermediate tubular handle 20 fixed or relatively fixed. Moreover, the inner tubular member 12 and the intermediate tubular member 14 may be moved in concert while keeping the outer tubular member 16 fixed or relatively fixed by manipulating the inner tubular handle 22 and in concert the intermediate tubular handle 20 while the outer tubular handle 18 keeping fixed or relatively fixed.

As depicted in FIG. 1, the system 10 advantageously includes a stent engaging member 28 disposed to or at the distal end of the intermediate tubular member 14, and a stent holder 26 disposed on the inner tubular member 12. The stent holder 26 is disposed distally away from the stent engaging member 28 when intermediate handle 20 is proximally placed toward the outer handle 18. As described below, the stent engaging member 28 is useful for engaging a proximal end of a stent and compressingly loading the stent into the system 10 through axial manipulation of the system 10, for example by axial movement of intermediate handle 20. The stent holder 26 is useful for securing the stent 30 within the system 10, for example, against the outer tubular member 16, until delivery of the stent 30 is desired within a bodily lumen (not shown).

As depicted in FIG. 1, the system 10 may further include a distal tip 24 disposed at the distal end of the inner tube 12. The distal tip 24 is useful for navigating bodily lumens without causing trauma to the same.

The tubular members 12, 14, 16 are formed of a body compatible material. Desirably, the biocompatible material is a biocompatible polymer. Examples of suitable biocompatible polymers include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. Desirably, the biocompatible polymers include polypropylene (PP), polytetrafluoroethylene (PTFE), polyethylene terephthalate (PET), high density polyethylene (HDPE), combinations and copolymers thereof, and the like. Materials for the tubular members 12, 14, 16 may be the same or different.

The tubular members 12, 14, 16, may also have a surface treatment and/or coating on their inner surface, outer surface or portions thereof. A coating need not be applied to all of the tubular members 12, 14, 16, and individual members may be coated, uncoated, partially coated, and the like. Useful coating materials include any suitable biocompatible coating. Non-limiting examples of suitable coatings include polytetrafluoroethylene, silicone, hydrophilic materials, hydrogels, and the like. Useful hydrophilic coating materials include, but are not limited to, alkylene glycols, alkoxy polyalkylene glycols such as methoxypolyethylene oxide, polyoxyalkylene glycols such as polyethylene oxide, polyethylene oxide/ polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly (vinylsulfonic acid), acryl amides including poly(N-alkylacrylarnide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride, combinations and copolymers thereof, and the like. Additional details of suitable coating materials and methods of coating medical devices with the same may be found in U.S. Pat. Nos. 6,447,835 and 6,890,348, the contents of which are incorporated herein by reference. Such coatings and/or surface treatment is desirably disposed on the inside or a portion thereof of the outer tubular member 16 to aid, if desired, in loading and/or deploying of the stent 30.

FIG. 2 illustrates a radially self-expanding stent 30 that can be radially compressed and loaded into system 10, transluminally delivered to an intended intraluminal treatment site, then released from the system for radial self-expansion against surrounding tissue. While the present invention can be applied to the delivery of many intraluminary devices, it is particularly suited for delivering the self-expanding stent 30. Desirably, the stent 30 is capable of being radially compressed and longitudinally extended for implantation into a bodily lumen. The degree of elongation depends upon the structure and materials of the stent 30 and may be quite varied. The diameter of the stent 30 also may become several times smaller as it elongates. It is preferred that the stent 30 be constructed to self-expand when released from a radially compressed state. Any stent that is capable of radial expansion may be used in accordance with the present invention. For example, a radially distensible stent which does not substantially longitudinally elongate upon radial contraction is also useful. A non-limiting example of such a stent is one formed from zig-zag or undulating wires or wire. Thus, various stent types and stent constructions may be employed in the invention, and the invention can be constructed to accommodate stents of various sizes and configurations.

As depicted in FIG. 3, one embodiment of the present invention applies the method and system of the present invention to a braided stent 30. FIG. 3 is an exploded or enlarged view of the stent 30 to depict the braiding of the stent filaments 32. As used herein the term braiding and its variants refer to the diagonal intersection of elongate filaments 32 so that each filament passes alternately over and under one or more of the other filaments, which is commonly referred to as an intersection repeat pattern. Useful braiding patterns include, but are not limited to, a diamond braid having a 1/1 intersection repeat pattern, a regular braid having a 2/2 intersection repeat pattern or a hercules braid having a 3/3 intersection repeat pattern. The passing of the filaments under and over one and the other results in slidable filament crossings that are not interlooped or otherwise mechanically engaged or constrained.

While the stent 30 may be formed of metals, plastics or other materials, it is preferred that a biocompatible material or construction is employed. Useful biocompatible materials include, but are not limited to, biocompatible metals, biocompatible alloys, biocompatible polymeric materials, including synthetic biocompatible polymeric materials and bioabsorbable or biodegradable polymeric materials, materials made from or derived from natural sources and combinations thereof. Useful biocompatible metals or alloys include, but not limited to, nitinol, stainless steel, cobalt-based alloy such as Elgiloy, platinum, gold, titanium, tantalum, niobium, polymeric materials and combinations thereof. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks and polytetrafluoroethylenes. The polymeric materials may further include a metallic, a glass, ceramic or carbon constituent or fiber. Useful and nonlimiting examples of bioabsorbable or biodegradable polymeric materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Further, the stent 30 may include materials made from or derived from natural sources, such as, but not limited to collagen, elastin, glycosaminoglycan, fibronectin and laminin, keratin, alginate, combinations thereof and the like.

Further, the stent 30 may be made from polymeric materials which may also include radiopaque materials, such as metallic-based powders or ceramic-based powders, particulates or pastes which may be incorporated into the polymeric material. For example, the radiopaque material may be blended with the polymer composition from which the polymeric wire is formed, and subsequently fashioned into the stent as described herein. Alternatively, the radiopaque material may be applied to the surface of the metal or polymer stent. Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent 30 may be selectively made radiopaque at desired areas along the stent or made be fully radiopaque, depending on the desired end-product and application. Further, portions of the stent 30, for example stent filaments, may have an inner core of tantalum, gold, platinum, iridium or combination of thereof and an outer member or layer of nitinol to provide a composite filament for improved radiocapicity or visibility. Alternatively, the stent 30 may also have improved external imaging under magnetic resonance imaging (MRI) and/or ultrasonic visualization techniques. MRI is produced by complex interactions of magnetic and radio frequency fields. Materials for enhancing MRI visibility include, but not be limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the stent 30 of the present invention may include ultrasound resonant material, such as but not limited to gold. Other features, which may be included with the stent 30 of the present invention, include radiopaque markers; surface modification for ultrasound, cell growth or therapeutic agent delivery; varying stiffness of the stent or stent components; varying geometry, such as tapering, flaring, bifurcation and the like; varying material; varying geometry of stent components, for example tapered stent filaments; and the like.

Figures 4, 5, 6:
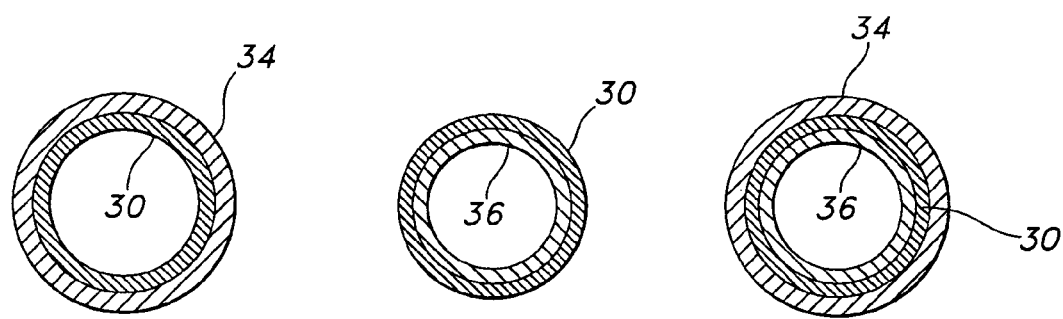
FIG. 4 is a cross-sectional view of the stent of FIG. 3 illustrating an outer graft covering disposed on the stent.
FIG. 5 is a cross-sectional view of the stent of FIG. 3 illustrating an inner graft lining disposed on the stent.
FIG. 6 is a cross-sectional view of the stent of FIG. 3 illustrating an inner graft lining and an outer graft covering disposed on the stent.

Also, the stent 30 may have coverings, films, coatings, and the like disposed over, under or throughout or embedding the stent 30. For example, as depicted in FIG. 4, the stent 30 may include a covering 34, desirably a polymeric covering, disposed over the longitudinal length or a portion of the longitudinal length of the stent 30. Further, as depicted in FIG. 5, the stent 30 may include a liner 36, desirably a polymeric liner, disposed within the longitudinal length or a portion of the longitudinal length of the stent 30. Moreover, as depicted in FIG. 6, the stent 30 may include a both a covering 34 and a liner 36, desirably a polymeric covering and liner which include the same or different polymeric materials, disposed over and within the longitudinal length or a portion of the longitudinal length of the stent 30. The covering and the liner of FIG. 6 may be a unitary film or coating that embeds or partially embeds the stent 30. The covering 34 and/or the liner 36 may be in the form of a tubular structure, for example composed of polymeric material and/or silicone. The covering 34 and/or the liner 36 may also comprise any plastic or polymeric material, desirably a somewhat hard but flexible plastic or polymeric material. The covering 34 and/or the liner 36 may be transparent or translucent, desirably substantially or partially transparent. Furthermore, the covering 34 and/or the liner 36 may be constructed of any suitable biocompatible materials, such as, but not limited to, polymers and polymeric materials, including fillers such as metals, carbon fibers, glass fibers or ceramics. Useful covering 34 and/or the liner 36 materials include, but are not limited, polyethylene, polypropylene, polyvinyl chloride, polytetrafluoroethylene (PTFE), including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, silicones, and copolymers and combinations thereof. The coating or coatings may be on the stent 30, components of the stent 30, and combinations thereof. The stent components, in part or in total, may be temporary, for example bioabsorbable, biodegradable, and the like, or may be permanent (i.e., not substantially bioabsorbable or biodegradable), for example the above-described biocompatible metals, alloys and polymers.

Desirably, the stent 30 includes braided polyester filaments, such as PET polyester filaments. Further, in some application, the stent 30 is desirably embedded in a coating of silicone. Additional details of such desirable stents are described in U.S. Pat. No. 6,162,244, the contents of which are incorporated herein by reference.

Further, the stent 30 may be treated with a therapeutic agent or agents, such as, but not limited to, anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Figure 7:
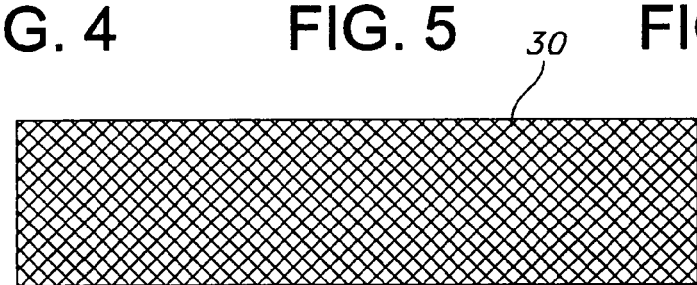
FIG. 7 is a side planar view of the stent of FIG. 2 illustrating a substantially longitudinally straight stent.
Figure 8:
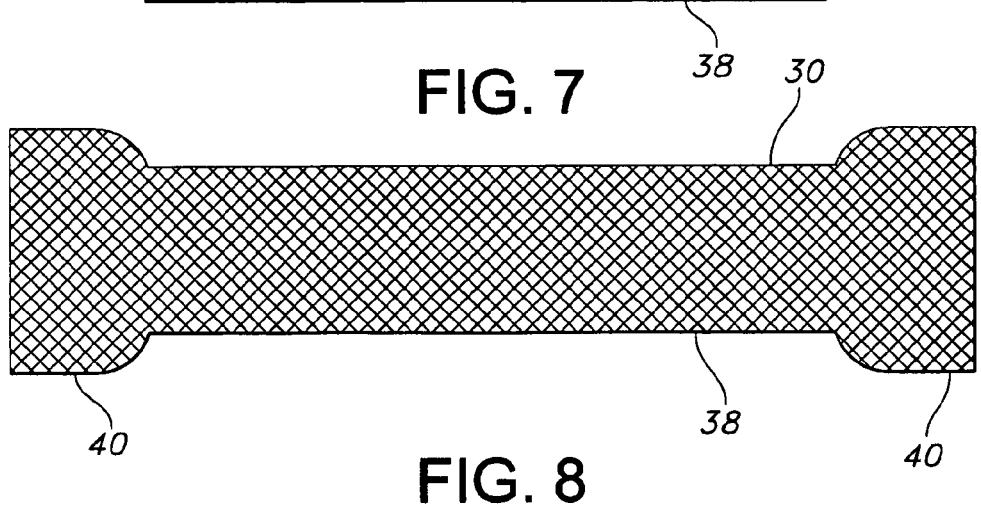
FIG. 8 is a side planar view of a stent illustrating outwardly flared ends according to the present invention.

Further, as depicted in FIG. 7, the stent 30 may have a straight or substantially straight longitudinal portion 38. The present invention, however, is not so limited. For example, the stent 30 may have a varied diameter, such as a flaring or tapering, along a portion or portion of its longitudinal expanse. One non-limiting example of a varied diameter stent 30 is depicted in FIG. 8. The stent 30 of FIG. 8 may include a longitudinal length 38 and one or two flared ends 40. As depicted in FIG. 8, the flared ends 40 are enlarged flared ends having a diameter greater than the diameter of the longitudinal portion 38 of the stent 30. The stent 30, however, is not so limited, and for example the flared ends 40, individually or in combination, may have a smaller diameter that the diameter of the longitudinal portion 38 of the stent 30. Further, the stent 30 may be repositionable, removable and/or reconstrainable, and/or may include multiple interconnected or non-interconnected stents. For example, the stent 30 may include a loop or element, such as a suture loop or element, a polymeric loop or element, metallic or element, and combinations thereof which may be accessible to a user or practitioner, for example by the use of forceps, to reposition, remove and/or reconstrain the stent 30 after it has been delivered, partially or totally, to a bodily lumen. Moreover, a loop or element may be integrally formed as part of the stent 30. Further details of useful repositioning, removing and/or reconstraining loops or elements may be found in U.S. patent application Ser. No. 11/341,540, filed Jan. 27, 2006 and entitled "Stent Retrieval Member And Devices And Methods For Retrieving Or Repositioning A Stent" and in U.S. patent application Ser. No. 11/432,065, filed May 11, 2006, and entitled "Integrated Stent Respostioning And Retrieval Loop", the contents of both of which are incorporated herein by reference.

Returning to FIGS. 1 and 2, the inner tubular member 12 may include a first tubular or distal portion 12' and a second tubular or proximal portion 12". The distal portion 12' desirably has a larger diameter that the proximal portion 12" such that the proximal portion 12" is slidably disposed within the intermediate handle 20 while the distal portion 12' is slidable through only a portion of the intermediate handle 20. In such a case, the intermediate handle 20 may have a distal opening 42 larger than a proximal opening 44. Such an arrangement servers, as described below, may function as a stop or limit for the axial movement of distal portion 12' of the inner tubular member 12 relative to the intermediate tubular member 14 during loading of the stent 30.

FIG. 2 depicts the stent 30 loading position for the system 10 of the present invention. The handles 18 and 20 are disposed relatively towards one and the other such that the stent engaging member 28 is exposed and having its distal portion radially extended to a diameter larger, for example substantially larger, than the outside diameter of the outer tubular member 16, for example at least about double the diameter. The stent engaging member 28, which is depicted as being in the shape of a funnel, may be bonded, crimped or otherwise secured to the distal end of the intermediate member 14. Desirably, the engaging member 28 has a truncated-conical shape, outwardly diverging in the distal direction from its proximal end, e.g., the proximal end being smaller than the distal end. The proximal end has a diameter equal or substantially equal, including slightly larger, to the diameter of the intermediate tubular member 14, but less than the diameter of the outer tubular member 16.

The engaging member 28 may be formed of a thin polymeric film, for example, but not limited to, polyamide, such as polyamide 6-6 or nylon, PET or PTFE. The film is desirably compliant, so that the funnel is capable of alternatively assuming an open configuration as seen in FIG. 1 for receiving a proximal end of stent 30, and a collapsed configuration to allow engaging member 28 to be accommodated or contained within outer tubular member 16. Desirably, the engaging member 28 is resilient and tends to assume the open configuration in the relaxed state when free of external stresses. Alternatively, the engaging member 28 may be pliable, in particular radially distensible, mesh, weave or braid. The engaging member 28 may be of any reasonable length and/or diameter to permit the loading of the stent 30. The engaging member 28 may have a beveled edge or profile for easier loading, removing or repositioning of the stent 30. Further, the engaging member 28 may only partially circumferentially surround or encompass the intermediate tubular member 14. Still further, the engaging member 28 may be split or slit at either or both of its distal and proximal ends. Moreover, the engaging member 28 may comprise a film with pores. Furthermore, the intermediate tubular member 14, and optionally including the engaging member 28 and/or the intermediate handle 20, may be removable from the device or system 10. For example, after loading the stent 30 into the device or system 10, the intermediate tubular member 14 may be pulled proximally and removed from between the inner and outer tubular members 12, 16. For example, the intermediate tubular member 14, and optionally the engaging member 28 and/or the intermediate handle 20, may be split and pulled away from the inner tubular member 12. In such a case, the intermediate tubular member 14, and optionally the engaging member 28 and/or the intermediate handle 20, may be releasably disposed within the device or system 10.

After the proximal end of the stent 30 is placed with the stent engaging member 28, as depicted in FIG. 2, the stent 30 may be squeezed or radially contacted onto or about the inner tubular member 12 and pushed into the intermediate tubular member 14 which is disposed substantially within the outer tubular member 16. The stent 30 may be manually manipulated to load the stent 30 into the intermediate tubular member 14. Alternatively, the stent 30 may be disposed within a loading cartridge (not shown) for facilitating storage and delivery of the stent 30 into the intermediate tubular member 14. The loading cartridge may contain a piston or other axially movable member to facilitate stent movement. Details of suitable stent loading cartridges are further described in U.S. Pat. No. 6,068,635 and/or U.S. Patent Application Publication 2003/0083730 A1, the contents of which are incorporated herein by reference. During the loading of the stent 30, the handles 18 and 20 may be kept in relative constant axial displacement from one and the other. As such, the inner tubular member 12 and the intermediated tubular member 14 are also kept in relative constant axial positions with the intermediate tubular member 14 being substantially disposed within the outer tubular member 16. The intermediate tubular member 14 need not be completely contained within the outer tubular member 18, but rather a portion of the distal end of the intermediate tubular member 14 may be axially outside or distally disposed from the distal end of the outer tubular member 16. The smaller distal opening 42 of the intermediate handle 20 serves as a stop or an axially limiting device to keep the intermediate and inner tubular members 14, 12 in relative constant axial arrangement during loading of the stent 30. To complete the stent 30 loading, the inner handle 22 is pulled away from the outer handle 18 to complete the loading.

As depicted in FIG. 9, the stent 30 is fully loaded into the system 10 of the present invention. As described above, the inner handle 22 is pulled away axially away from the outer handle 18 in the stent loaded position as compared the handle 18, 22 positions of FIGS. 1 and 2. In other words, the outer tubular member 16 is advanced distally toward the distal tip 24 to cover the stent 30. The stent holder 26 releasably secures the stent 30 between the inner tubular member 12 and the outer tubular member 16. Desirably, the stent holder 26 is a hollow tubular band. More desirably, the stent holder 26 is a hollow tubular band that is free or substantially free of barbs, pins or protrusions which may engage and possible damage the stent 30. The stent holder 26 may be made of any suitable polymeric, rubber or metallic material. Moreover, the stent holder 26 may have a pattern, such as a surface pattern of indentations and/or protrusions, for facilitating securement of the stent 30. In some embodiments, the stent holder 26 may have barbs, pins or protrusions which may engage the stent 30. Further, with any of the embodiments, the device or system 10 may include multiple stent holders 26, either axially spaced apart or axially juxtaposed. Further, the stent holder 26 may not have to completely encompass the inner tubular member 12, but may be only partially disposed around a circumferential portion of the inner tubular member 12.

As depicted in FIG. 10, after the stent 30 is loaded or completely loaded or contained within the outer tubular member 16, the intermediate handle 20 is advance proximally away from the outer handle 18 and proximally toward the inner handle 22. The stent engaging member 28 is moved axially away from the loaded stent 30. In other words, the proximal end of the loaded stent 30 is now free from the stent engaging member 28. Such removal of the stent loading member 28 from the loaded stent 30 facilitates delivery of the stent 30 as less force will be required to deploy the stent 30.

As depicted in FIG. 11, the loaded stent 30 may be delivered to a bodily lumen (not shown) by advancing the outer handle 18 and correspondingly the outer tubular member 16 axially away from the distal tip 24. In other words, the outer tubular member 16 is retracted in a proximally axial direction to delivery the stent 30. As depicted in FIGS. 10-11, the intermediate handle 20 and the inner handle 22 may be proximally and/or juxtaposingly disposed during certain stages of loading, constraining and/or deploying the stent 30. Accordingly, the stent loading member handle 20 may be integrated, for example mechanically integrated, with the inner tubular handle 22 to permit concurrent or simultaneous movement of the two handles 20, 22. Such mechanical integration, if desired, may be achieved by matching and/or interlocking detents (not shown) on the two handles 20, 22. The mechanical integration may be achieved through the use of releasably interlocking detents (not shown) on the two handles 20, 22 to permit, when desired, independent movement of the two handles 20, 22 by mechanically releasing the detents from one and another and to permit, when desired, concurrent or simultaneous movement of the two handles 20, 22 by mechanically engaging the detents with one and another.

FIG. 12 is an enlarged view of an embodiment of the proximal portion of the system 10 of the present invention. A step or cut-away portion of the inner tubular member 12 may optionally serve as the above-described proximal portion 12'. As described, such a proximal portion 12' in conjunction with the small proximal opening 44 of the intermediate handle 20 serves as a stop during loading of the stent 30 into the system 10 of the present invention. The present invention, however, is not so limited. For example, as depicted in FIG. 13, in another embodiment the distal and proximal openings 42, 44 of the intermediate handle 20 may be the same, substantially the same or about the same. In such a case, the intermediate handle 20 may be temporarily held against or near the outer handle 20 during loading of the stent 30 into the system 10.

Figure 14:
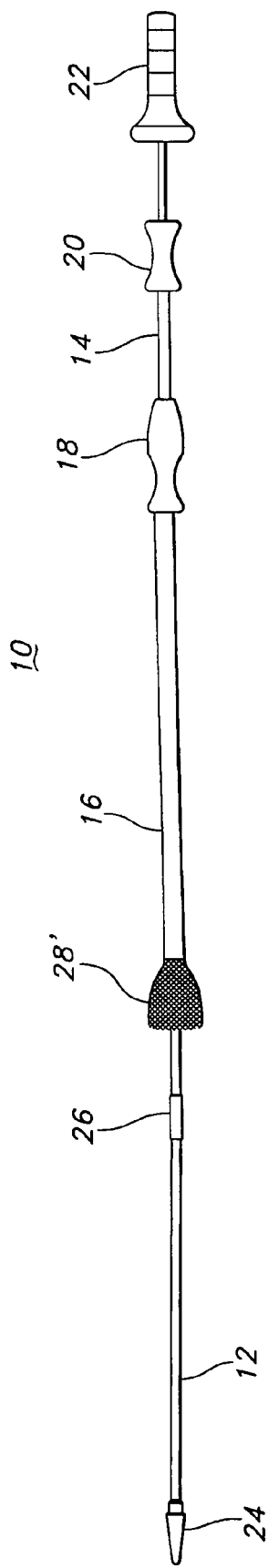
FIG. 14 is a top planar view of the stent loading and delivery device or system of the present invention.
Figure 15:
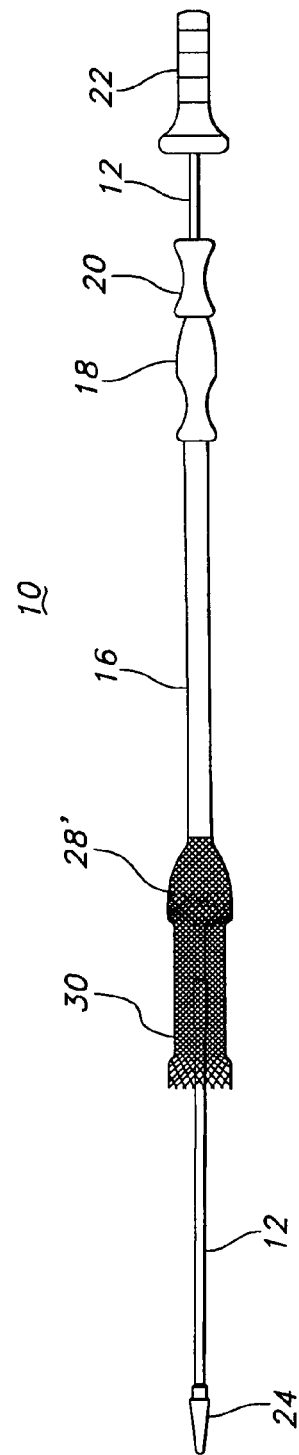
FIG. 15 is a top planar view of the stent loading and delivery device or system of FIG. 14 illustrating initial loading of a tapered stent.

FIGS. 14 and 15 are a top planar view of the system 10' of the present invention. This embodiment is substantially similar to the embodiment depicted in FIGS. 1 and 2, except for the stent engaging member 28'. The stent engaging member 28' is a radially distensible basket, which can be made of similar materials or different materials of the stent 30. As depicted in FIGS. 16-17, the stent engaging member 28' has a truncated-conical shape 46, outwardly diverging in the distal direction from its proximal end, which then merges, desirably seamlessly, into a straight or substantially straight cylindrical portion or rim portion 48. The stent engaging member 28' may be radially distensible, i.e., it tends to assume an enlarged state when released from a contracted state, such as being compressed within the outer tubular member 16. The stent engaging member 28' is especially useful for engaging the stent 30 having an outwardly extending end 40. As depicted in FIG. 19, the stent engaging member 28'' may be simply made radially distensible and a truncated-conical shape by compressing a proximal portion of cylindrical stent engaging member 28' onto the inner tubular member 14. Additionally, a portion 48' of the rim portion 48 of the stent engaging member 28''' may be inwardly biased, as depicted in FIG. 20. Such alternate stent engaging designs 28', 28'', 28''' are useful with the different stent configurations described herein.

FIG. 18 is a top planar view of the different elements of the system 10' of the present invention in an "unassembled" stage. The inner tubular member 12 is the longest member. The intermediate tubular member 14 is smaller than the inner tubular member 12, but longer than the outer tubular member 16. Finally, the outer tubular member 16 is typically the shortest of the members. The present invention, however, is not so limited and other tube length configurations may suitably be selected.

Figure 21:
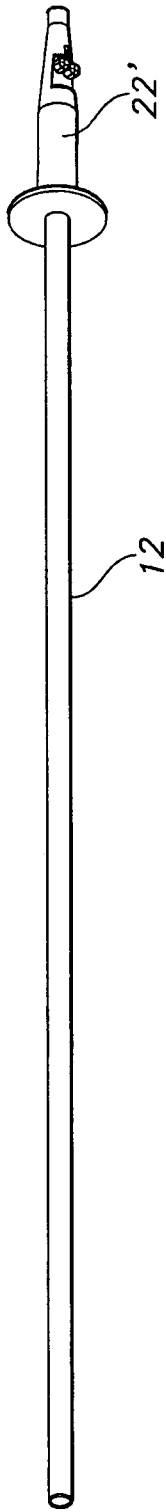
FIGS. 21-23 depict an alternate embodiment of a handle for the delivery device of the present invention.
Figure 22:
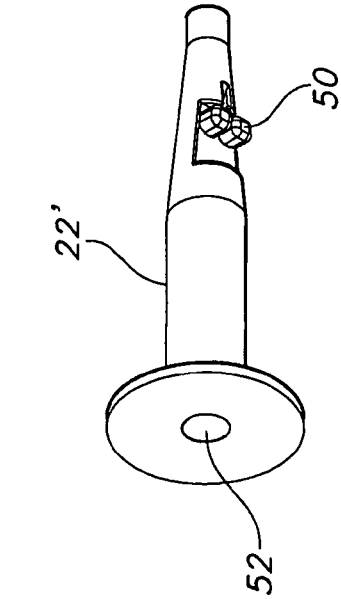
Figure 23:
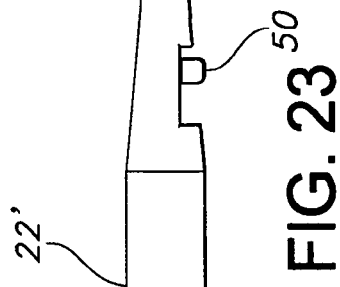

Moreover, the inner tubular member 22 may be modified to enhance repositioning and/or retrieval of the stent 30. For example as depicted in FIGS. 21-23, the inner tubular handle 22' may include prongs 50. Prongs 50 are useful for securing a suture thread (not shown) to the outside of the handle 22'. The suture thread (not shown) may then be disposed within the cavity or lumen 50 of the handle 22'. The suture thread may then be disposed within a lumen or cavity of the inner tubular member 12 and exit at an intermediate point whereby the suture thread may be secured to the stent 30. The suture thread may be manipulated by the user to reposition and/or the stent during or after delivery of the stent 40. Upon completion of the stent delivery, the suture thread may be removed, for example by cutting, from the stent 30. Such additional features are further described in U.S. application Ser. No. 11/437,455, entitled "Apparatus and Method for Loading and Delivering a Stent", filed on same date herewith and, U.S. application Ser. No. 11/437,459, entitled "Apparatus and Method for Loading and Delivering a Stent Using a Suture Retaining Mechanism", filed on same date herewith, the contents of which are incorporated herein by reference.

Figure 24:
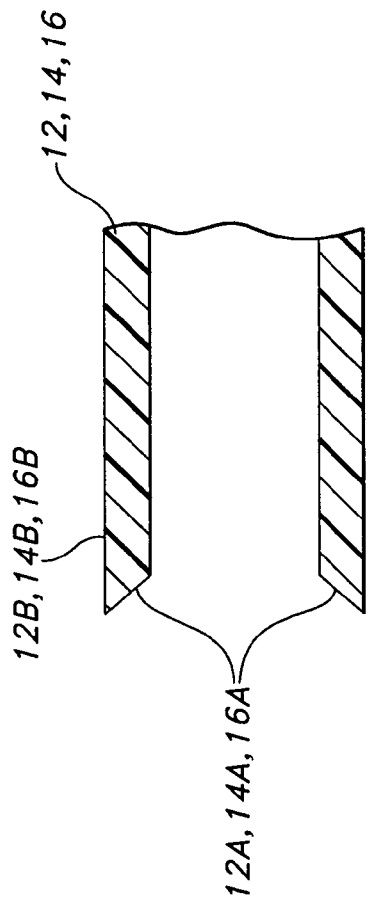
FIG. 24 is a cross-section view of a distal end on a tubular member of the device or system of FIG. 1 illustrating an inwardly beveled edge or end thereat.

Further, the tubular members 12, 14, 16, may have a beveled or slanted edge at their distal end, proximal end or combinations thereof. For example, as depicted in FIG. 24, tubular members 12, 14, 16, may have an inwardly beveled edge 12A, 14A, 16A at their respective distal ends 12B, 14B, 16B. Desirably, the beveled edge 16A is an inwardly beveled edge on the distal end 16B of the outer tubular member 16. Such beveled edges, in particular beveled edge 16A, are useful in aiding the loading and/or deployment of the stent 30. As depicted in FIG. 24, an inwardly beveled edge or end is where the wall of the tubular member has a greater longitudinal expanse at its outer wall portion as compared to its inner wall portion. Desirably, such beveled edges are smooth edges and accordingly may include rounded or smoothly contoured portions.

A feature of the present invention is that the stent loading is reversible. Suppose the user suspects that stent 30 was incorrectly positioned during loading, or determines that a different stent should be used. Stent 30 is easily unloaded, by operating handles 20 and 22 to advance inner tubular member 12 toward the open position. This progressively releases stent 30 from the outer tubular member 16, whereupon the stent 30 may be removed from stent engaging member 28 by hand.

Another feature of the present invention is that the stent holder 26 is distally spaced apart from the stent engaging member 28. Such axial displacement allows the stent holder 26 to releasably hold the stent 30 within the system 10 even after the stent engaging member 28 is axially displaced away from the stent 30. Such a feature allows, if desired, for a large portion of the stent 30 to be deployed and then be recaptured by the device 10 prior to complete deployment of the stent 30. Such recapturing may be achieved with the above-described suture thread or by axially sliding the outer tubular member 16 over the stent 30. Moreover, the stent engaging member 28 may be repositioned within the inner tubular member 12 and the outer tubular member 16, for example, by axially advancing the member 28 to reposition the stent 30 therein between. Furthermore, the whole device 10 may be moved proximally or distally to reposition the stent 30 therein.

These features provide, among other things, reconstrainability of the stent 30 within the system or device 10 of the present invention. For example, the outer tubular member 16 may be advanced over the stent 30 to a location distally past the tubular band 26 to releasably and securably set the position of the stent engaging member 28 and/or the stent loading member 14 relative to the position of the inner tubular member 12. The outer tubular member 16 may be retracted proximally past the tubular band 26, thereby allowing repositioning of the stent 30 within the outer tubular member 16 and/or over the inner tubular member 12. The outer tubular member 16 may be re-advanced over the stent 30 and the tubular band 26 to releasably and securably reset the position of the stent engaging member 28 and/or the stent loading member 14 relative to the position of the inner tubular member 12, thereby allowing reconstrainment of the stent.

In one aspect of the present invention a stent loading and deployment device 10 is provided. The device 10 includes an outer elongate tubular member 16 having opposed proximal and distal ends; an inner elongate tubular member 12 having opposed proximal and distal ends and slidably disposed within the outer tubular member 16, wherein, when the distal ends of the outer tubular member 16 and the inner tubular member 12 are axially aligned, a stent deployment region 13 is defined there in between; and a stent loading member 14 having opposed proximal and distal ends and slidably disposed between the outer tubular member 16 and the inner tubular member 12. Desirably, the distal end of the stent loading member 14 is slidable to a distal position past the distal end of the outer tubular member 16 for receiving a stent 30 and is further slidable toward the proximal end of the outer tubular member 16 to a location past the stent deployment region 13 for disengagement of a stent 30 from the stent loading member 14.

The device 10 may further include a stent engaging member 28 having opposed proximal and distal ends. Desirably, the proximal end is securably disposed to the distal end of the stent loading member 14. The stent engaging member 28 may have a truncated-conical shape, being smaller at its proximal end, i.e., outwardly diverging in a distal direction from its proximal end. The stent engaging member 28 may be a thin film which is collapsible such that the stent engaging member 28 may be slidably contained within the outer tubular member 16, or may be a radially distensible member 28', 28", 28''' which is collapsible such that the stent engaging member 28', 28", 28''' may be slidably contained within the outer tubular member 16. Desirably, the stent engaging member is a polymeric member 28, 28', 28", 28'''. The stent engaging member 28', 28", 28''' may include, in part or substantially, braided filaments. The braided filaments may include polymeric filaments, metallic filaments and any other suitable filaments. The braided filaments may be contained within a thin polymeric film. Desirably, the stent loading member 14 is an elongate tubular device.

The device 10 may further include a tubular band 26 disposed toward the distal end of the inner tubular member 12 for releasably securing a stent 30 in the stent deployment region 13 between the inner and outer tubular members 12, 16. Desirably, the outer tubular member 16 is slidable toward a distal position for releasing a stent 30 from the stent deployment region 13.

The device 10 may further include an outer tubular handle 18 disposed at the distal end of the outer tubular member 16; an inner tubular handle 22 disposed at the proximal end of the inner tubular member 12; and a stent loading member handle 20 disposed at the proximal end of the stent loading member 14. The stent loading member handle 20 may be axially disposed between the outer tubular handle 18 and the inner tubular handle 22. The outer member handle 18 may be axially disposed before the proximal end of the inner tubular member 12.

The device 10 of this aspect is useful containing and releasing a radially distensible stent 30. The radially distensible stent 30 may be a polymeric stent, including a braided stent. A graft, such as a covering, a liner, a film, a coating and combinations thereof, may be disposed over at least a portion of the stent. Desirably, the stent 30 is a braided polymeric stent and the graft is a silicone coating or film.

The features of this aspect of the present invention may suitably be combined in any combination according the present invention. In other words, all possible combinations of the features or elements of this aspect of the present invention are contemplated, including all features and elements described in conjunction with the drawings.

In another aspect of the present invention, a stent loading and deployment system 10 is provided. The system includes a radially distensible stent 30; an outer elongate tubular member 16 having opposed proximal and distal ends; an inner elongate tubular member 12 having opposed proximal and distal ends and slidably disposed within the outer tubular member 16, wherein, when the distal ends of the outer tubular member 16 and the inner tubular member 12 are axially aligned, a stent deployment region 13 is defined there in between; and a stent loading member 14 having opposed proximal and distal ends and slidably disposed between the outer tubular member 16 and the inner tubular member 12; wherein the distal end of the stent loading member 14 is slidable to a distal position past the distal end of the outer tubular member 16 for receiving the stent 30 and is further slidable toward the proximal end of the outer tubular member 16 to a location past the stent deployment region 13 for disengagement of the stent 30 from the stent loading member 14. Moreover, the features and/or elements of the earlier aspect of the present invention may suitably be combined in any combination to this aspect of the present invention.

Use of the device 10 is also contemplated by the present invention. Use of the device 10 may include a method for loading a stent 30 into a delivery and deployment device 10, which includes providing a radially distensible stent 30 having opposed proximal and distal ends; providing a delivery deployment device 10, the device 10 including an outer elongate tubular member 16 having opposed proximal and distal ends; an inner elongate tubular member 12 having opposed proximal and distal ends and slidably disposed within the outer tubular member 16, wherein, when the distal ends of the outer tubular member 16 and the inner tubular member 12 are axially aligned, a stent deployment region 13 is defined there in between; a stent loading member 14 having opposed proximal and distal ends and slidably disposed between the outer tubular member 16 and the inner tubular member 12; and optionally a stent engaging member 28 having opposed proximal and distal ends, wherein the proximal end of the stent engaging member 28 is securably disposed to the distal end of the stent loading member 14; axially moving or sliding the distal end of the stent loading member 14 to a distal position past the distal end of the outer tubular member 16; optionally engaging the proximal end of the stent 30 with the stent engaging member 28; axially moving or sliding the stent 30 and the stent loading member 14 toward the proximal end of the outer tubular member 16 to radially compress the stent 30 within the stent deployment region 13; and optionally axially moving or sliding the stent engaging member 28 to a location past the stent deployment region 13 for disengagement of the stent 30 from the stent loading member 14. The method or use may further include providing a tubular band 26 disposed toward the distal end of the inner tubular member 12 for releasably securing the stent 30 in the stent deployment region 13 between the inner and outer tubular members 12, 16. Moreover, the method may further include axially moving or sliding the outer tubular member 16 toward a proximal position for releasing the stent 30 from the stent deployment region 13. The method or use may yet further include providing an outer tubular handle 18 disposed at the proximal end of the outer tubular member 16; providing an inner tubular handle 22 disposed at the proximal end of the inner tubular member 12; and providing a stent loading member handle 20 disposed at the proximal end of the stent loading member 14, wherein independent axial movement of the outer tubular member 16, the inner tubular member 12 or the stent loading member 14 is achieved by manual manipulation of the handles 18, 22, 20.

Additionally, the outer tubular member 16 may be advanced over the stent 30 to a location distally past the tubular band 26 to releasably and securably set the position of the stent engaging member 28 and/or the stent loading member 14 relative to the position of the inner tubular member 12. Further, the outer tubular member 16 may be retracted proximally past the tubular band 26, thereby allowing repositioning of the stent 30 within the outer tubular member 16 and/or over the inner tubular member 12. The outer tubular member 16 may be re-advanced over the stent 30 and the tubular band 26 to releasably and securably reset the position of the stent engaging member 28 and/or the stent loading member 14 relative to the position of the inner tubular member 12, thereby allowing reconstrainment of the stent.

While various embodiments of the present invention are specifically illustrated and/or described herein, it will be appreciated that modifications and variations of the present invention may be effected by those skilled in the art without departing from the spirit and intended scope of the invention.

What is claimed is:

1. A stent loading and deployment device comprising:
   an outer elongate tubular member having opposed proximal and distal ends and a length therein between;
   an outer tubular handle disposed at the proximal end of the outer tubular member;
   an inner elongate tubular member having opposed proximal and distal ends, a length therein between and slidably disposed within the outer tubular member, wherein when the distal ends of the outer tubular member and the inner tubal member are axially aligned, a stent deployment region is defined therein between;
   an inner tubular handle disposed at the proximal end of the inner tubular member;
   a stent loading member having opposed proximal and distal ends, a length therein between and slidably disposed between the outer tubular member and the inner tubular member;
   a stent loading member handle disposed at the proximal end of the stent loading member; and
   a stent engaging member having opposed proximal and distal ends, wherein the proximal end of the stent engaging member is securably disposed to the distal end of the stent loading member;
   wherein the stent engaging member has a truncated-conical shape, being smaller at its proximal end;
   wherein the stent engaging member is a radially distensible member which is collapsible such that the stent engaging member may be slidably contained within the outer tubular member;
   wherein the distal end of the stent loading member is slidable to a distal position past the distal end of the outer tubular member for receiving a stent and is further slidable toward the proximal end of the outer tubular member to a location past the stent deployment region for disengagement of a stent from the stent loading member;
   wherein the length of the stent loading member is greater than the length of the outer elongate tubular member;
   wherein the inner elongate tubular member comprises a distal portion and a proximal portion with the distal portion having a greater diameter than the proximal portion, and
   wherein the proximal portion of the inner elongate tubular member is slidable throughout the stent loading member handle while the distal portion of the inner elongate tubular member is slidable through only a portion of the stent member handle.

2. The device of claim 1, wherein the stent engaging member is a polymeric member.

3. The device of claim 2, wherein the stent engaging member comprises braided filaments.

4. The device of claim 2, wherein the stent engaging member comprises a film.

5. The device of claim 3, wherein the braided filaments are contained within a thin polymeric film.

6. The device of claim 1, wherein the stent loading member is an elongate tubular device.

7. The device of claim 1, wherein the stent loading member is removably disposed within the device.

8. The device of claim 1, further comprising a tubular band disposed toward the distal end of the inner tubular member for releasably securing a stent in the stent deployment region directly between the inner and outer tubular member;
   wherein the tubular band may partially or completely encompass a portion of the inner tubular member.

9. The device of claim 1, wherein the outer tubular member is proximally slidable for releasing a stent from the stent deployment region.

10. The device of claim 1, wherein the stent loading member handle is axially disposed between the outer tubular handle and inner tubular handle.

11. The device of claim 1, wherein the stent loading member handle is integrated with the inner tubular handle.

12. The device of claim 10, wherein the outer tubular handle is axially disposed before the proximal end if the inner tubular handle.

13. The device of claim 1, wherein the stent loading member handle, the outer tubular handle or the inner tubular handle are interlocking handles.

14. The device of claim 1, further including a radially distensible stent.

15. The device of claim 14, wherein the radially distensible stent is a polymeric stent.

16. The device of claim 14, wherein the radially distensible stent is a self-expanding stent.

17. The device of claim 15, wherein the polymeric stent is a braided stent.

18. The device of claim 14, further comprising a graft disposed over at least a portion of the stent.

19. The device of claim 18, wherein the graft is selected from the group consisting of a covering, a liner, a film, a coating and combinations thereof.

20. The device of claim 19, wherein the stent is a braid polymeric stent and the grate comprises silicone.

21. A stent loading and deployment system comprising:
    a radially distensible stent;
    an outer elongate tubular member having opposed proximal and distal ends and a length therein between;
    an outer tubular handle disposed at the proximal end of the outer tubular member;
    an inner elongate tubular member having opposed proximal and distal ends, a length therein between and slidably disposed within the outer tubular member, wherein, when the distal ends of the outer tubular member and the inner tubular member are axially aligned, a stent deployment region is defined therein between;
    an inner tubular handle disposed at the proximal end of the inner tubular member;

a stent loading member having opposed proximal and distal ends, a length therein between and slidably disposed between the outer tubular member and the inner tubular member;

a stent loading member handle disposed at the proximal end of the stent leading member; and a stent engaging member having opposed proximal distal ends, wherein the proximal end of the stent engaging member is securably disposed to the distal end of the stent loading member;

wherein the stent engaging member has truncated-conical shape, being smaller at its proximal end;

wherein the stent engaging member is radially distensible member which is collapsible such that the stent engaging member may be slidably contained within the outer tubular member;

wherein the distal end of the stent loading member is slidable to a distal position past the distal end of the outer tubular member for receiving the stent and is further slidable toward the proximal end of the outer tubular member to a location past the stent deployment region for disengagement of the stent from the stent loading member;

wherein the length of the stent loading member is greater than the length of the outer elongate tubular member;

wherein the inner elongate tubular member comprises a distal portion and a proximal portion with the distal portion having a greater diameter than the proximal portions; and wherein the proximal portion of the inner elongate tubular member is slidable throughout the stent loading member handle while the distal portion of the inner elongate tubular member is slidable through only a portion of the stent loading member handle.

22. The system of claim 21, wherein the stent engaging member is polymeric member.

23. The system of claim 22, wherein the stent engaging member comprises braid filaments.

24. The system of claim 23, wherein the stent engaging member comprises a film.

25. The system of claim 24, wherein the braided filaments are contained within a thin polymeric film.

26. The system of claim 21, wherein the radially distensible stent is a polymeric stent.

27. The system of claim 21, wherein the radially distensible stent is a self-expanding stent.

28. The system of claim 21, wherein the polymeric stent is a braided stent.

29. The system of claim 21, further comprising a tubular band disposed toward the distal end of the inner tubular member for releasably securing the stent in the stent deployment region directly between the inner and outer tubular members;
wherein the tubular band may partially or completely encompass a portion of the inner tubular member.

30. The system of claim 21, wherein the stent loading member handle is axially disposed between the outer tubular handle and the inner tubular handle;
and wherein the outer tubular handle is axially disposed before the proximal end of the inner tubular handle.

31. The system of claim 21, wherein the stent loading member handle is integrated with the inner tubular handle.

32. The system of claim 21, wherein the stent loading member handle, the outer tubular handle or the inner tubular handle are interlocking handles.

33. A stent loading and deployment system comprising:
a radially distensible stent;
an outer elongate tubular member having opposed proximal and distal ends and a length therein between;

an outer tubular handle disposed at the proximal end of the outer tubular member;

an inner elongate tubular member having opposed proximal and distal ends, a length therein between and slidably disposed within the outer tubular member, wherein, when the distal ends of the outer tubular member and the inner tubular member are axially aligned, a stent deployment region is defined therein between;

an inner tubular handle disposed at the proximal end of the inner tubular member;

a stent loading member having opposed proximal and distal ends, a length therein between and slidably disposed between the outer tubular member and the inner tubular member;

a stent loading member handle disposed at the proximal and end of the stent loading member;

a stent engaging member having opposed proximal and distal ends, wherein the proximal end of the stent engaging member is securably disposed to the distal end of the stent loading member; and a tubular band disposed toward the distal end of the inner tubular member for releasably securing a stent in the stent deployment region directly between the inner and outer tubular members;

wherein the tubular band may partially or completely encompass a portion of the inner tubular member;

wherein the stent engaging member had a truncated-conical shape, being smaller at its proximal end;

wherein the stent engaging member is a radially distensible member which is collapsible such that the stent engaging member may be slidably contained within the outer tubular member;

wherein the distal end of the stent loading member is slidable to a distal portion past the distal end of the outer tubular member for receiving the stent and is further slidable toward the proximal end of the outer tubular member to a location past the stent deployment region for disengagement of the stent from the stent loading member;

wherein the length of the stent loading member is greater than the length of the outer elongate tubular member;

wherein the tubular band is disposed distally away from the stent holding member when the stent loading member handle is proximally placed towards the outer tubular handle;

wherein the inner elongate tubular member comprises a distal portion and a proximal portion with the distal portion having a greater diameter than the proximal portion;

wherein the stent loading member handle has a distal opening and a proximal opening with the distal opening being larger in diameter than the proximal opening; and wherein the proximal portion of the inner elongate tubular member is slidable through the distal and proximal openings of the stent loading member handle while the distal portion of the inner elongate tubular member is slidable through the distal opening of the stent loading member handle but not slidable through the proximal opening of the stent loading member handle.

34. The device of claim 1, wherein the stent loading member handle has a distal opening and a proximal opening with the distal opening being larger in diameter than the proximal opening; and
wherein the proximal portion of the inner elongate tubular member is slidable through the distal and proximal openings of the stent loading member handle while the distal portion of the inner elongate tubular member is slidable through the distal opening of the stent loading member handle, but not slidable through the proximal opening of the stent loading member handle.

35. The system of claim 21, wherein the stent loading member handle has a distal opening and a proximal opening with the distal opening being larger in diameter than the proximal opening; and wherein the proximal portion of the inner elongate tubular member is slidable through the distal and proximal openings of the stent loading member handle while the distal portion of the inner elongate tubular member is slidable through the distal opening of the stent loading member handle, but not slidable through the proximal opening of the stent loading member handle.

* * * * *

UNITED STATES PATENT AND TRADEMARK OFFICE
CERTIFICATE OF CORRECTION

| | | |
|---|---|---|
| PATENT NO. | : 8,535,368 B2 | Page 1 of 1 |
| APPLICATION NO. | : 11/437889 | |
| DATED | : September 17, 2013 | |
| INVENTOR(S) | : F. Anthony Headley, Jr. et al. | |

It is certified that error appears in the above-identified patent and that said Letters Patent is hereby corrected as shown below:

In the Claims

Column 19, Line 48, Claim 28, delete "21" and insert --26--.

Signed and Sealed this
Eighth Day of April, 2014

Michelle K. Lee
*Deputy Director of the United States Patent and Trademark Office*

UNITED STATES PATENT AND TRADEMARK OFFICE
CERTIFICATE OF CORRECTION

| | | Page 1 of 1 |
|---|---|---|
| PATENT NO. | : 8,535,368 B2 | |
| APPLICATION NO. | : 11/437889 | |
| DATED | : September 17, 2013 | |
| INVENTOR(S) | : Headley, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1436 days.

Signed and Sealed this
Twenty-fourth Day of February, 2015

Michelle K. Lee
*Deputy Director of the United States Patent and Trademark Office*